(12) United States Patent
Gabriel et al.

(10) Patent No.: US 7,049,051 B2
(45) Date of Patent: May 23, 2006

(54) PROCESS FOR FORMING AND ACOUSTICALLY CONNECTING STRUCTURES ON A SUBSTRATE

(75) Inventors: Kaigham J. Gabriel, Pittsburgh, PA (US); Xu Zhu, Pittsburgh, PA (US)

(73) Assignee: Akustica, Inc., Pittsburgh, PA (US)

( * ) Notice: Subject to any disclaimer, the term of this patent is extended or adjusted under 35 U.S.C. 154(b) by 119 days.

(21) Appl. No.: 10/349,618

(22) Filed: Jan. 23, 2003

(65) Prior Publication Data

US 2004/0146810 A1 Jul. 29, 2004

(51) Int. Cl.
*G03C 5/00* (2006.01)

(52) U.S. Cl. .................. 430/322; 430/323; 430/313; 430/317; 216/74; 216/79

(58) Field of Classification Search .............. 430/322, 430/323, 313, 317; 216/74, 79
See application file for complete search history.

(56) References Cited

U.S. PATENT DOCUMENTS

| | | | |
|---|---|---|---|
| 4,555,797 | A | 11/1985 | Nieuwendijk et al. |
| 5,658,710 | A | 8/1997 | Neukermans |
| 5,717,631 | A | 2/1998 | Carley et al. |
| 5,774,252 | A | 6/1998 | Lin et al. |
| 5,808,781 | A | 9/1998 | Arney et al. |
| 5,867,302 | A | 2/1999 | Fleming |
| 5,876,187 | A | 3/1999 | Afromowitz et al. |
| 5,949,892 | A | 9/1999 | Stewart |
| 5,970,315 | A | 10/1999 | Carley et al. |
| 6,028,331 | A | 2/2000 | Mastromatteo et al. |
| 6,128,961 | A | 10/2000 | Haronian |
| 6,255,757 | B1 | 7/2001 | Dhuler et al. |
| 6,262,946 | B1 | 7/2001 | Khuri-Yakub et al. |
| 6,386,507 | B1 | 5/2002 | Dhuler et al. |

2002/0011759 A1 * 1/2002 Adams et al. ............. 310/309

FOREIGN PATENT DOCUMENTS

| | | |
|---|---|---|
| EP | 0 911 952 A2 | 4/1999 |
| WO | WO 93/19343 A1 | 9/1993 |
| WO | WO 94/30030 A1 | 12/1994 |

OTHER PUBLICATIONS

Clarke, Peter, "English startup claims breakthrough in digital loudspeakers," EDTN network, EE Times online, pp. 1-5, 1999.

Iverson, Jon, "New Digital Loudspeaker Technology Announced from England," Stereophile News, pp. 1-2, 1999.

Iverson, Jon, "Just What Is a Digital Loudspeaker?," Stereophile News, pp. 1-3, 1999.

* cited by examiner

*Primary Examiner*—John A. McPherson
*Assistant Examiner*—Daborah Chacko-Davis
(74) *Attorney, Agent, or Firm*—Edward L. Pencoske

(57) ABSTRACT

The present invention describes a processes that builds an acoustic cavity, a chamber, and vent openings for acoustically connecting the chamber with the acoustic cavity. The dry etch processes may include reactive ion etches, which include traditional parallel plate RIE dry etch processes, advanced deep and inductively coupled plasma RIE processes. Three embodiments for connecting the chamber to the cavity from the top side of the substrate, e.g. by using pilot openings formed using at least a portion of the mesh as an etch mask, by forming the vent openings using at least a portion of the mesh as an etch mask, or by having the chamber intersect the vent openings as the chamber is being formed, illustrate how the disclosed process may be modified. By forming the cavity on the back side of the substrate, the depth of the vent holes is decreased. Additionally, using at least a portion of the micro-machined mesh as an etch mask for the vent holes makes the process self-aligning.

26 Claims, 7 Drawing Sheets

PROCESS FOR FORMING AND ACOUSTICALLY CONNECTING STRUCTURES ON A SUBSTRATE

BACKGROUND OF THE INVENTION

The present invention is directed generally to microelectromechanical Systems (MEMS) devices and, more particularly, to processes for forming chambers and cavities in a substrate and acoustically interconnecting such structures.

The ability to form moving parts measured in microns has opened up a huge range of applications. Such moving parts typically take the form of a beam or mesh that may form, for example, a variable capacitor, switch, or other component. The recent ability to seal micro-machined meshes has lead to the fabrication of microphones and microspeakers. See, for example, International Publication No. WO/01/20948 A2 published 22 Mar. 2001, entitled MEMS Digital-to-Acoustic Transducer With Error Cancellation, the entirety of which is hereby incorporated by reference.

A sealed mesh can function as a movable plate of a variable capacitor, and therefore can operate as a microphone. For a sealed mesh to operate as a microspeaker, the microspeaker needs to be able to push air to create a soundwave just as its larger counterparts must push air to create soundwaves. Traditional speaker enclosures have a port on the back to allow the speaker to move freely. In the case of a microspeaker, if the chamber beneath the sealed mesh does not have a vent or other opening to ambient, movement of the sealed mesh inward is inhibited by the inability to compress the air in the chamber while movement of the mesh outward is inhibited by formation of a vacuum. Thus it is necessary to form a vent in the chamber if the microspeaker is to create soundwaves.

Currently, such vents are formed by boring through the substrate from the rear. That requires patterning the back side of the substrate followed by an etch through the entirety of the substrate to reach the chamber. Forming of vents by this technique is slow in that several hundred microns of substrate may need to be etched to reach the chamber beneath the sealed mesh and the diameter of the vent is small compared to its depth. Additionally, there are registration problems in that it is necessary to work form the back side of the substrate where there are no landmarks, and hundreds of microns may need to be etched to reach a chamber that may measure in the tens of microns. Thus, the need exists for an easy, repeatable, fast process for forming vents in the chambers of sealed meshes that are to function as speakers.

BRIEF SUMMARY OF THE INVENTION

The present invention is directed to a process comprising reducing the thickness of a back side of a substrate in an area where vents are to be formed. A micro-machined mesh is released from a top side of the substrate. A vent opening is formed that connects the released mesh and the area of reduced thickness. Several embodiments of the invention are disclosed. In one embodiment, pilot openings are formed in the substrate in the area of reduced thickness by using at least a portion of the mesh as an etch mask. That assures proper alignment of the vent openings. Releasing of the mesh involves removal of a portion of substrate from beneath the mesh. While the mesh is being released, the vents are formed by expanding the size of the pilot openings.

According to another embodiment, the vent openings are formed after the mesh is released. In that embodiment, the mesh is released using an isotropic etch. After the mesh is released, the mesh is used as an etch mask for an anisotropic etch to form vent openings for connecting the chamber with the area of reduced thickness. Use of the mesh as an etch mask eliminates a lithography step and assures proper alignment of the vent openings.

According to another embodiment of the invention, vent openings are formed in the area of reduced thickness from the back side of the substrate using an anisotropic etch prior to releasing the mesh. When the mesh is released using an isotropic etch, during formation of the chamber under the mesh, the chamber intersects the vent openings.

A common step in the various embodiments of the invention is to reduce the thickness of the substrate in the area of the vent openings. That is accomplished by etching a large cavity; because the diameter of the cavity relative to the depth is large, this step can be carried out efficiently. Connecting to this cavity is accomplished from the top side of the substrate, e.g. by using pilot openings formed using at least a portion of the mesh as an etch mask, by forming the vent openings using the mesh as an etch mask, or by having the chamber intersect the vent openings as the chamber is being formed. Those embodiments that use the mesh as an etch mask eliminate a lithography step thereby increasing processing speeds. Those advantages and benefits, and others, will be apparent from the Detailed Description of the Invention herein below.

BRIEF DESCRIPTION OF THE DRAWINGS

For the present invention to be easily understood and readily practiced, the present invention will now be described, for purposes of illustration and not limitation, in conjunction with the following figures, wherein.

DETAILED DESCRIPTION OF THE INVENTION

Figure 1:
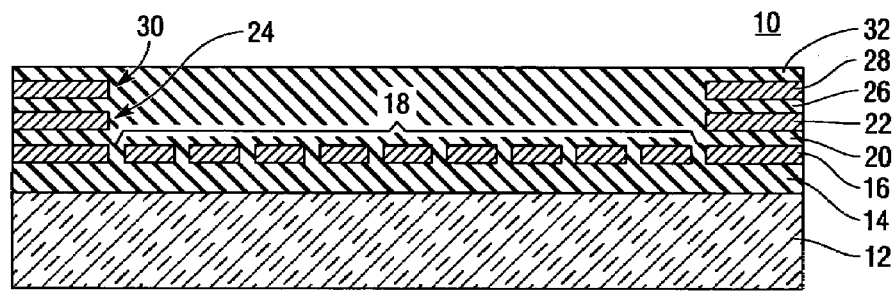
FIG. 1 illustrates a substrate having a plurality of metal layers patterned to form a device.

A first embodiment of the present invention is illustrated in conjunction with FIGS. 1–9. In FIG. 1, a die 10 is received from a CMOS foundry. At the CMOS foundry, a silicon substrate 12 has been processed so as to form alternating layers of, for example, a dielectric material and a metal. The die 10 illustrated in FIG. 1 has a first layer of dielectric material 14 carrying a first metal layer 16. The first metal layer 16 has been patterned such that a portion thereof forms a micro-machined mesh 18. Formed on the first metal layer 16 is a second layer of dielectric 20. The second layer of dielectric 20 carries a second metal layer 22 which has been patterned to have an opening 24 formed therein. The second metal layer 22 carries a third layer of dielectric 26. The third layer of dielectric 26 carries a third layer of metal 28 which has been patterned to have an opening 30 formed therein. A top layer of dielectric 32 is formed on top of the third metal layer 28.

The present invention is not limited to the position and configuration of the metal layers shown in the figures. For example, the pattern shown in FIG. 1 could be implemented in metal layers two, three and four such that references herein to a first, second and third layers of metal need not correspond to metal layers one, two and three, respectively. Additionally, the configuration of the layers of metal need not be as shown in the figures but rather may vary depending upon the device to be fabricated.

As previously mentioned, the die 10 would be received, for example, as shown in FIG. 1 from the CMOS foundry. Thereafter, the die 10 will be subjected to post-processing fabrication steps. Although it is anticipated that the post-processing fabrication steps will take place in a facility different from the CMOS foundry which fabricated the die 10, that is not a requirement of the present invention.

Figure 2:
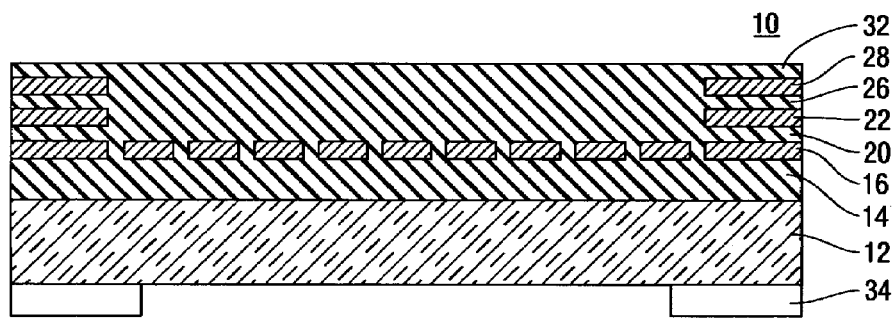
FIG. 2 illustrates the substrate of FIG. 1 after the back side has been patterned with a resist.

Turning to FIG. 2, a layer of resist 34 is formed on the back of the substrate 12 and patterned with a mask which is used to form an acoustic cavity. Those of ordinary skill in the art will realize that landmarks from the top side of the die 10 need to be transferred to the bottom side of substrate 12. Transferring such landmarks is known in the art are therefore not described herein.

Figure 3:
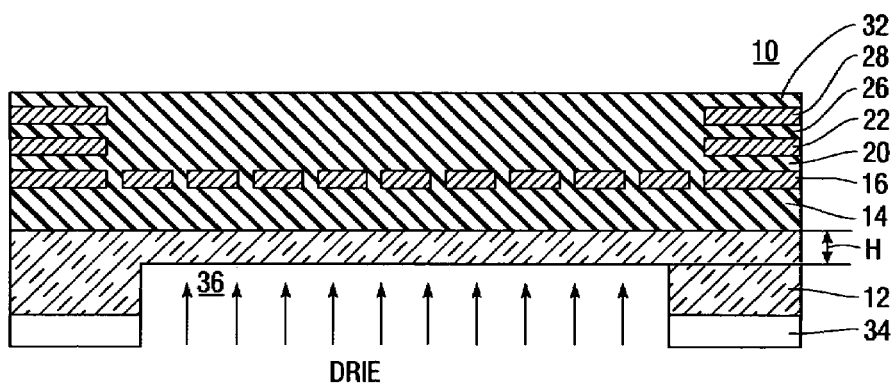
FIG. 3 illustrates the substrate of FIG. 2 having a cavity formed in the back side of the substrate as a result of an anisotropic etch.

In FIG. 3, the substrate 12 is subjected to an anisotropic etch. The anisotropic etch may be a dry, deep reactive ion etch (DRIE) into the substrate 12 to create an acoustic cavity 36. Etching stops at tens to hundreds of microns (dimension h in FIG. 3) before the substrate-dielectric interface.

Figure 4:
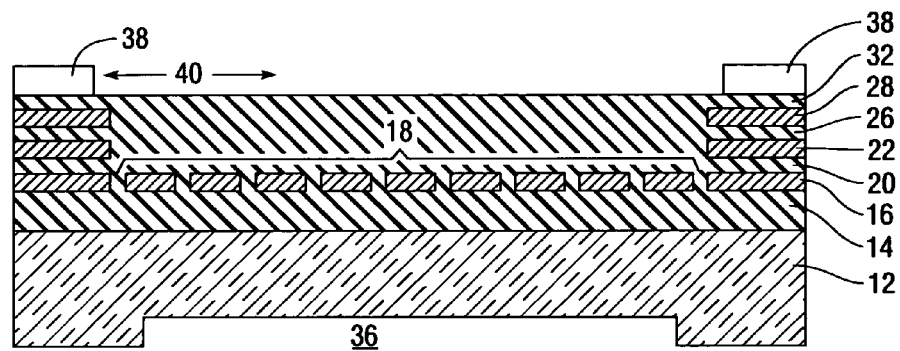
FIG. 4 illustrates the substrate of FIG. 3 after the resist on the back side has been removed and the top side has been patterned with a resist.
Figure 5:
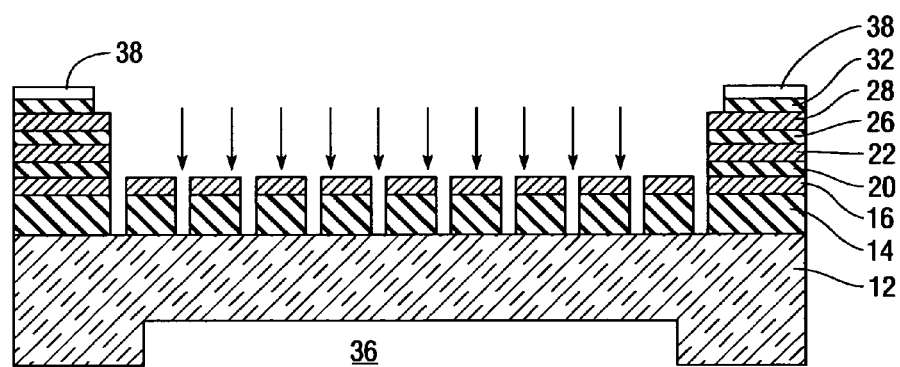
FIG. 5 illustrates the substrate of FIG. 4 after an anisotropic etch has been performed.

FIG. 4 illustrates the substrate 12 of FIG. 3 after the resist on the back side of the substrate 12 has been removed and a new layer of resist 38 formed on the top side and patterned to provide an opening 40 in the area of the mesh 18. In FIG. 5, the substrate 12 of FIG. 4 is illustrated being subjected to an anisotropic RIE dry etch through the dielectric layers 32, 26, 20 and 14. The patterned resist 38 and the first metal layer 16 are used to pattern the first dielectric layer 14. The layer of resist 38 may not be necessary if it is not necessary to protect the top layer of dielectric 32.

Figure 6:
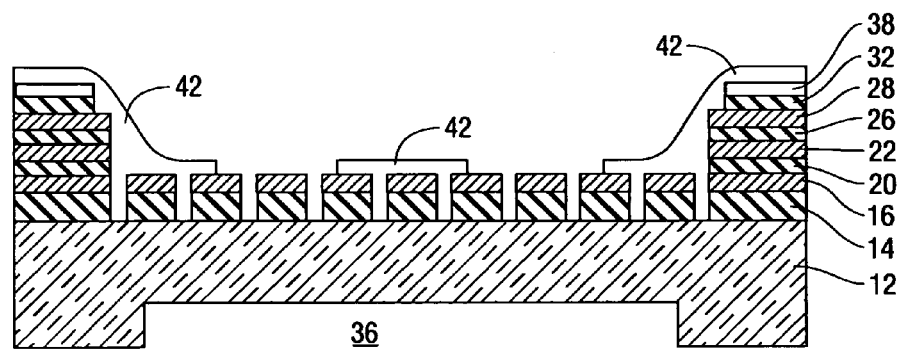
FIG. 6 illustrates the substrate of FIG. 5 after the top side has been patterned with a resist to enable certain portions of the mesh to act as an etch mask for pilot openings to be formed in the substrate in the area of the cavity.
Figure 7:
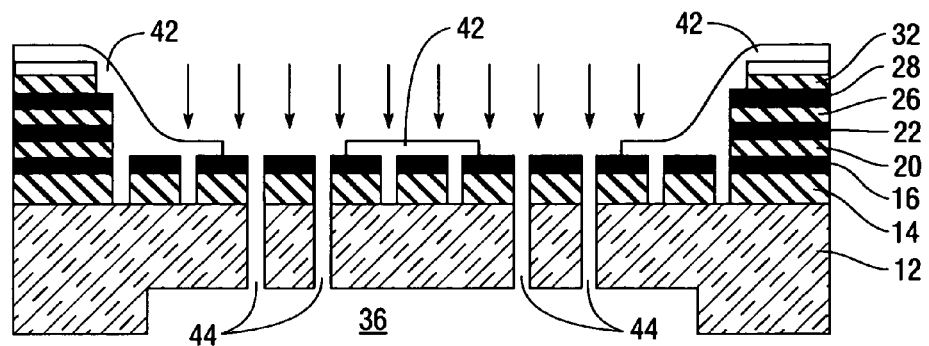
FIGS. 7 and 7A illustrate the substrate of FIG. 6 after pilot openings have been formed as a result of an anisotropic etch.
Figure 8:
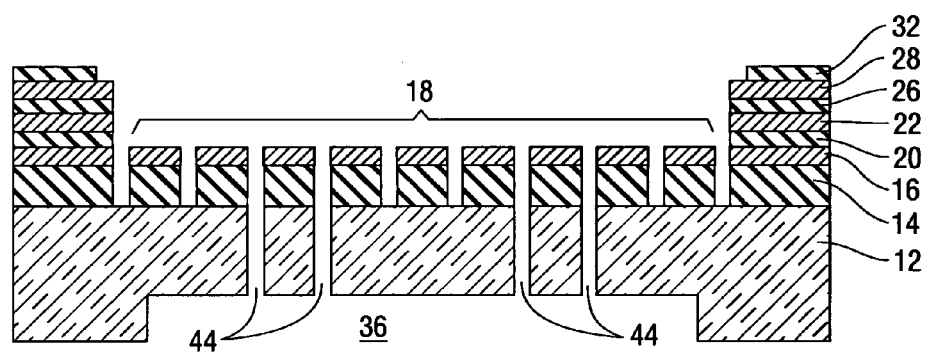
FIGS. 8 and 8A illustrate the substrate of FIGS. 7 and 7A, respectively, after the resist has been removed from the top side of the substrate.
Figure 7A:
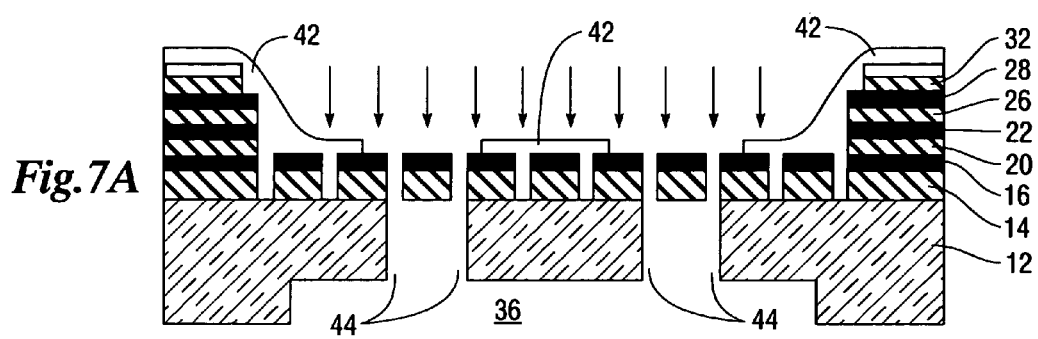
Figure 8A:
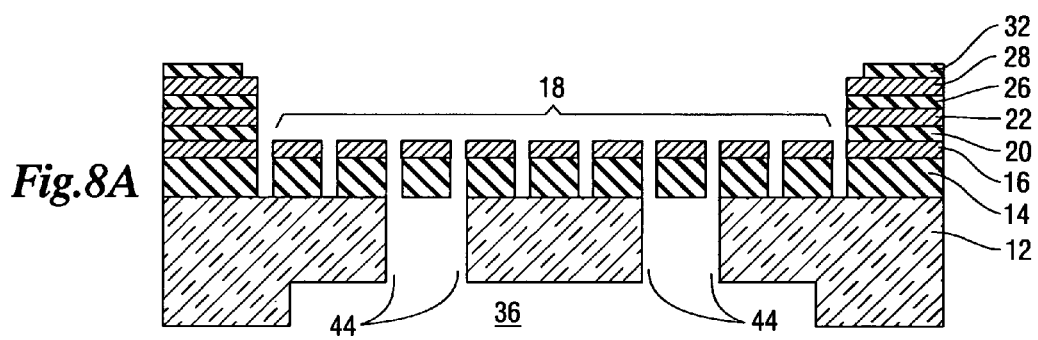

FIG. 6 illustrates the substrate of FIG. 5 after the top side has been patterned with a layer of resist 42 to enable certain portions of the mesh 18 to act as an etch mask for pilot openings to be formed in the substrate 12 in the area of the cavity 36. FIG. 7 illustrates the substrate 12 of FIG. 6 being subjected to a DRIE anisotropic etch which forms pilot openings 44 extending through the silicon substrate 12 in the area of the cavity 36. FIG. 7A illustrates the same step of the process as FIG. 7. However, in FIG. 7A it is assumed that the width of the mesh is much smaller (eg. 0.6 microns) then the depth of the reduced substrate (eg. 100 microns). Under these circumstances, formation of the pilot holes 44 may result in formation of vent openings. FIGS. 8 and 8A show the substrate 12 of FIGS. 7 and 7A, respectively, after the resist 42 has been removed.

Figure 9:
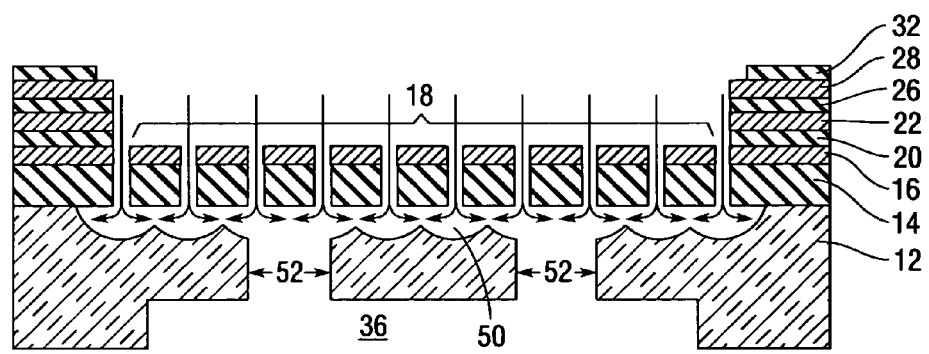
FIGS. 9 and 9A illustrate the substrate of FIGS. 8 and 8A, respectively, after the top side has been patterned with a resist and a chamber is formed under the mesh as a result of an isotropic etch.
Figure 9A:
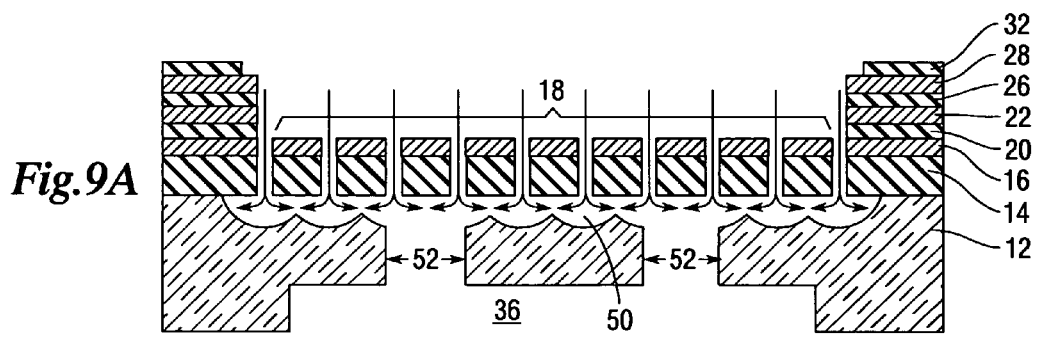

FIGS. 9 and 9A illustrate the substrate of FIGS. 8 and 8A, respectively, being subjected to an isotropic etch so as to form a chamber 50 under the mesh 18. Forming the chamber 50 releases the mesh 18 from substrate 12. In FIG. 9, as the chamber 50 is being formed, the pilot holes 44 are being enlarged to form vent openings 52. In FIG. 9A, the already formed vent holes are enlarged. Thus in the embodiment of the invention illustrated in FIGS. 1–9, at substantially the same time that the chamber 50 is being formed, the chamber 50 is being connected to the cavity 36 by the formation or enlargement of vent openings 52. Because the vent openings 52 are formed by enlarging the pilot openings 44, and the pilot openings 44 are formed by using a portion of the mesh 18 as an etch mask, the vent openings 52 will be in alignment so as to connect chamber 50 with cavity 36.

Figure 10:
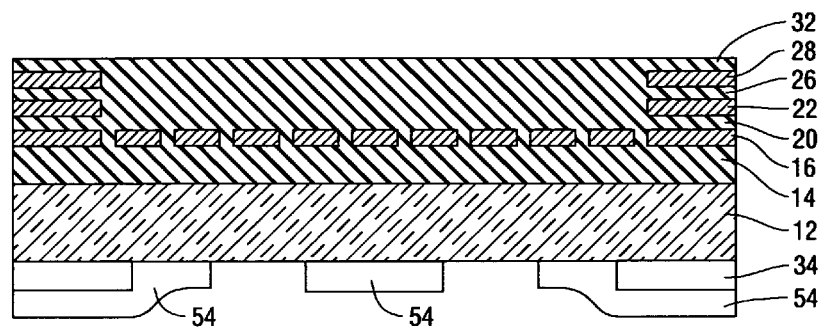
FIG. 10 illustrates the substrate of FIG. 2 after a second layer of resist has been deposited and patterned on the back side of the substrate.

FIGS. 10–15 illustrate another embodiment of the present invention. FIG. 10 illustrates the substrate of FIG. 2 after a second layer of resist 54 has been deposited on the back side of the substrate and patterned in a manner, as described below, for forming acoustic cavity 36 and vent openings 52. Those of ordinary skill will recognize that whether two separate layers 34, 54 are used, the positions of layers 34, 54 are reversed, or one layer is used, are not material to the present invention as long as resist is provided in any manner to provide the function described below.

Figure 11:
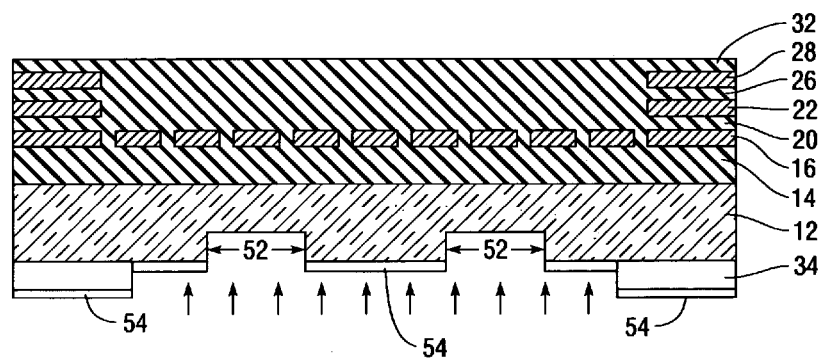
FIGS. 11 and 12 illustrate the progression of an anisotropic etch performed on the back side of the substrate to form a cavity and vent openings.
Figure 12:
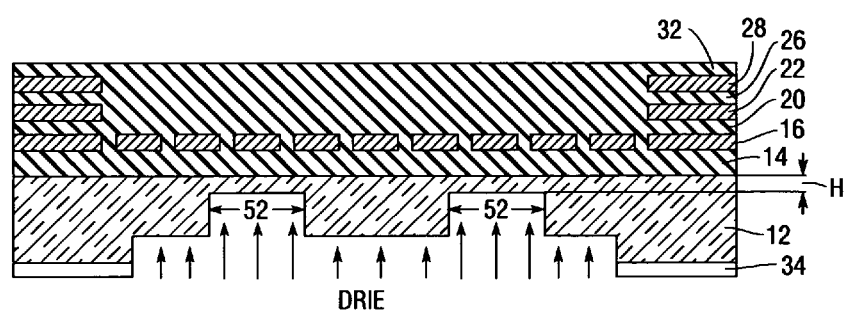

FIGS. 11 and 12 illustrate the progression of an anisotropic etch performed on the back side of the substrate 12. The etch may be a DRIE and, as the etch progresses, the resist layer 54 is progressively removed. As the layer 54 is progressively removed, vent openings 52 are being formed. Eventually, layer 54 is entirely removed and, as the etch progresses, cavity 36 is formed while the depth of vent openings 52 continues to increase. During this time, a portion of resist layer 34 may be removed as shown in FIG. 12. The etch may be stopped anywhere from a few ten to one hundred microns below the dielectric-silicon interface (h in FIG. 12).

Figure 13:
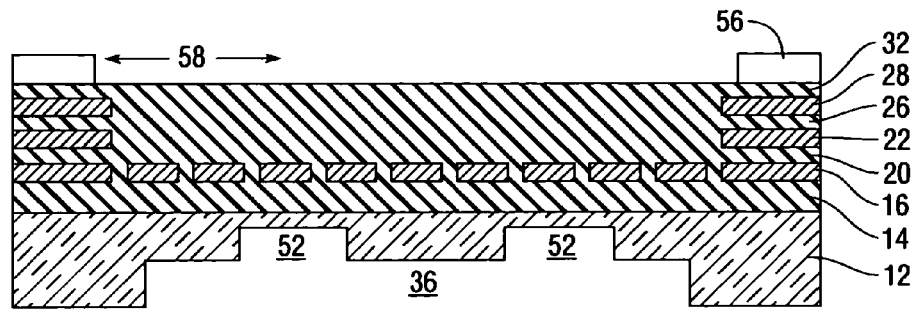
FIG. 13 illustrates the substrate of FIG. 12 after the resist has been removed from the back side and the top side has been patterned with a resist.

FIG. 13 illustrates the substrate 12 of FIG. 12 after the resist 34 has been removed from the back side of the substrate 12 and the top side has formed thereon a layer of resist 56 having an opening 58 formed therein. The opening 58 is designed to expose the mesh 18. Depending upon the need to protect the top layer of dielectric 32, applying and patterning the layer of resist 56 may not be necessary.

Figure 14:
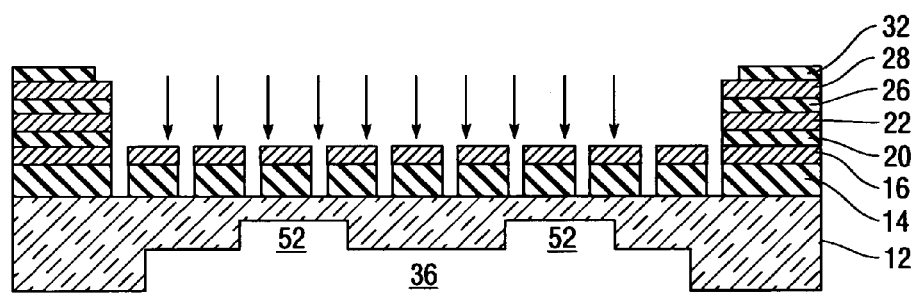
FIG. 14 illustrates the substrate of FIG. 13 after an anisotropic etch has been performed and the resist removed from the top side.

FIG. 14 illustrates the substrate 12 of FIG. 13 after an anisotropic etch of the dielectric material. Additionally, in FIG. 14, the resist 56 has been removed.

Figure 15:
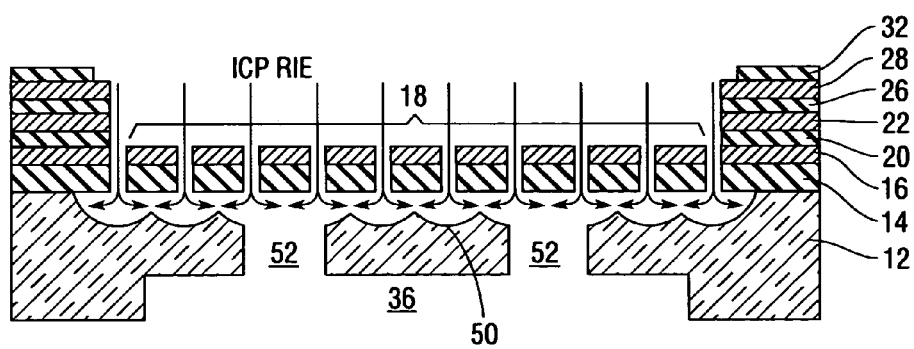
FIG. 15 illustrates the substrate of FIG. 14 after an isotropic etch has been performed to form a chamber under the mesh; during formation of the chamber, the chamber intersects the vent openings.

In FIG. 15, an isotropic etch of the silicon substrate 12 is performed to remove material from underneath the mesh 18 to thereby release the mesh 18. The removal of material from underneath the mesh 18 forms a chamber 50. As the chamber 50 is being formed, it intersects the vent openings 52.

Figure 16:
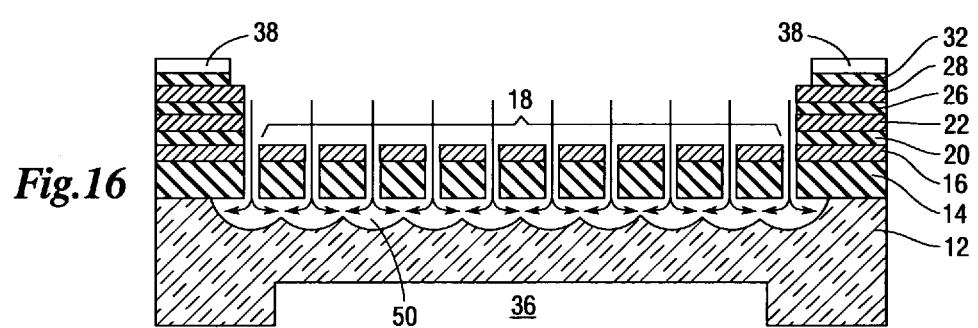
FIG. 16 illustrates the substrate of FIG. 5 after an isotropic etch has been perform to form a chamber under the mesh.
Figure 17:
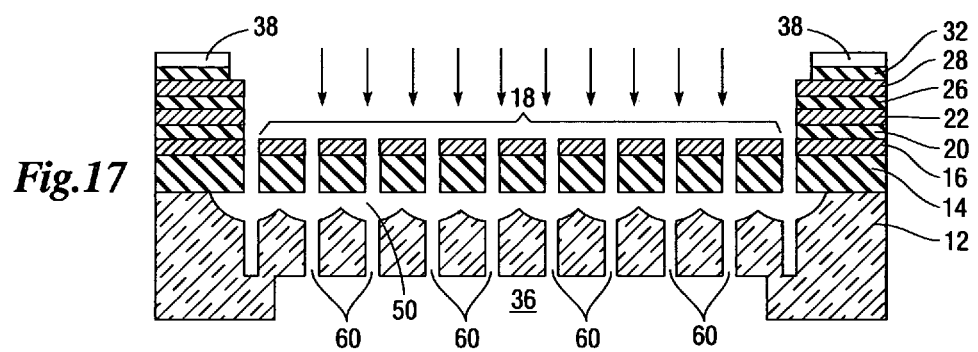
FIG. 17 illustrates the substrate of FIG. 16 after an anisotropic etch has been performed to form vent openings using the mesh as an etch mask.

FIGS. 16 and 17 illustrate another embodiment of the present invention. In FIG. 16, the substrate of FIG. 5 is illustrated. However, instead of performing the anisotropic etch illustrated in FIG. 5, an isotropic etch is performed. For example, an inductively coupled plasma (ICP) RIE may be performed. The isotropic etch illustrated in FIG. 16 forms a chamber 50 under the mesh 18 thereby releasing the mesh 18. Thereafter, in FIG. 17, an anisotropic etch, such as a DRIE etch, is performed using the mesh 18 as an etch mask. The anisotropic etch of FIG. 17 forms a plurality of vent openings 60 connecting chamber 50 with acoustic cavity 36. Those of ordinary skill in the art will recognize that when the mesh 18 is used as an etch mask, that saves a lithography step as a resist layer does not need to be formed and patterned to guide the etch process.

Completing the process, the mesh 18 of FIG. 9, the mesh 18 of FIG. 15, or the mesh 18 of FIG. 17 may be sealed using known deposition techniques to form a membrane capable of operating as a speaker or a microphone.

The present invention describes a set of dry etch processes that build an acoustic cavity 36, a chamber 50, and vent openings 52, 60 for acoustically connecting the chamber 50 with the acoustic cavity 36. The dry etch processes may use reactive ion etches, which include traditional parallel plate RIE dry etch processes, advanced deep and inductively coupled plasma RIE processes. The three embodiments of the present invention illustrate how the present invention may be modified to achieve the result of forming a chamber under a micro-machined mesh, to thereby release the mesh, and acoustically connecting that chamber with an acoustic cavity formed on the back side of the substrate. By forming the cavity on the back side of the substrate, the depth of the vent holes is decreased. Additionally, using the micro-machined mesh as an etch mask for the vent holes makes the process self-aligning.

While the present invention has been described in connection with preferred embodiments thereof, those of ordinary skill in the art will recognize that many modifications and variations are possible. The present invention is intended to be limited only by the following claims and not by the foregoing description which is intended to set forth the presently preferred embodiments.

What is claimed is:

1. A process, comprising:
   reducing the thickness of a back side of a substrate in an area where vents are to be formed;
   releasing a mesh from a top side of the substrate with an isotropic etch; and
   forming vent openings that connect the released mesh and the area of reduced thickness.

2. The process of claim 1 additionally comprising:
   forming pilot openings in said substrate in said area of reduced thickness by using said mesh as an etch mask; and
   wherein said forming is performed substantially simultaneously with said releasing.

3. The process of claim 2 additionally comprising applying and patterning a layer of resist to select certain portions of the mesh to act as said etch mask.

4. The process of claim 2 wherein an anisotropic etch is used to form said pilot openings and an isotropic etch is used for forming the vent openings.

5. The process of claim 1 wherein said forming is performed after said releasing.

6. The process of claim 5 wherein said forming comprises using said mesh as an etch mask.

7. The process of claim 6 wherein an anisotropic etch is used for said forming.

8. The process of claim 1 wherein said forming is performed from the back side of the substrate before said releasing.

9. The process of claim 8 wherein an anisotropic etch is used for said forming.

10. A process of forming and connecting structures on a substrate, comprising:
    forming an acoustic cavity from the back side of a substrate;
    forming a chamber under a micro-machined mesh from the top side of the substrate; and
    acoustically connecting the chamber with the acoustic cavity.

11. The process of claim 10 additionally comprising:
    forming pilot openings in said substrate in an area where said acoustic cavity is located by using said mesh as an etch mask; and
    wherein said forming a chamber comprises removing a portion of substrate from beneath the mesh, and
    wherein said connecting comprises using said pilot openings to form vent openings substantially simultaneously with said forming a chamber.

12. The process of claim 11 additionally comprising applying and patterning a layer of resist to select certain portions of the mesh to act as said etch mask.

13. The process of claim 11 wherein an anisotropic etch is used to form said pilot openings and an isotropic etch is used for forming the chamber and to form the vent openings.

14. The process of claim 10 wherein said connecting is performed after said forming a chamber.

15. The process of claim 14 wherein said connecting comprises using said mesh as an etch mask to form vent openings.

16. The process of claim 15 wherein an isotropic etch is used for forming the chamber and an anisotropic etch is used to form said vent openings.

17. The process of claim 10 wherein said connecting comprises forming vent openings from the back side of the substrate before forming said chamber, and
    wherein forming said chamber comprises removing a portion of substrate from beneath the mesh, and
    wherein said connecting comprises said chamber intersecting said vent openings during the forming of said chamber.

18. The process of claim 17 wherein an anisotropic etch is used for forming said vent openings and an isotropic etch is used for forming said chamber.

19. A process, comprising:
    forming a chamber under a micro-machined mesh; and
    substantially simultaneously with the formation of said chamber, connecting said chamber with a cavity formed on the back side of a substrate.

20. The process of claim 19 wherein said connecting comprises forming vent openings between the chamber and the cavity.

21. The process of claim 20 wherein said forming a chamber and forming vent openings comprises an isotropic etch.

22. The process of claim 19 additionally comprising forming vent openings from the back side of the substrate in the cavity, and wherein said connecting comprises said chamber intersecting said vent openings during said chamber formation.

23. The process of claim 22 wherein said forming a chamber and said connecting comprises an isotropic etch.

24. A process of acoustically connecting a chamber formed under a micro-machined mesh with a cavity formed on the back side of a substrate, comprising:

etching from the top side of the substrate to connect the chamber with the cavity.

25. The process of claim 24 wherein said etching includes forming vent openings in the substrate in the area of the cavity by using the micro-machined mesh as an etch mask.

26. The process of claim 25 wherein said etching includes an anisotropic etch.

* * * * *

UNITED STATES PATENT AND TRADEMARK OFFICE
CERTIFICATE OF CORRECTION

PATENT NO. : 7,049,051 B2 Page 1 of 1
APPLICATION NO. : 10/349618
DATED : May 23, 2006
INVENTOR(S) : Kaigham J. Gabriel and Xu Zhu It is certified that error appears in the above-identified patent and that said Letters Patent is hereby corrected as shown below:

Title Pg, Item (57) Abstract, Line 1, delete "processes" and substitute therefore --process--.

Column 1, Line 43, delete "form" and substitute therefore --from--.

Column 4, Line 15, delete "then" and substitute therefore --than--.

Signed and Sealed this

Seventeenth Day of June, 2008

JON W. DUDAS
*Director of the United States Patent and Trademark Office*